United States Patent [19]
Lloyd et al.

[11] Patent Number: 5,957,124
[45] Date of Patent: *Sep. 28, 1999

[54] DYNAMIC PARTICLE SIZE CONTROL FOR AEROSOLIZED DRUG DELIVERY

[75] Inventors: Lester J. Lloyd, Orinda; Peter M. Lloyd, Oakland; Reid M. Rubsamen; Jeffrey A. Schuster, both of Berkley, all of Calif.

[73] Assignee: Aradigm Corporation, Hayward, Calif.

[ * ] Notice: This patent is subject to a terminal disclaimer.

[21] Appl. No.: 08/534,786

[22] Filed: Sep. 27, 1995

Related U.S. Application Data

[63] Continuation-in-part of application No. 08/313,461, Sep. 27, 1994, Pat. No. 5,522,385.

[51] Int. Cl.$^6$ .................................................. A61M 11/00
[52] U.S. Cl. ............................... 128/200.22; 128/200.14; 128/204.23
[58] Field of Search ..................... 128/200.14, 200.22, 128/203.13, 204.23; 222/95; 239/102.2, 145

[56] References Cited

U.S. PATENT DOCUMENTS

| | | | |
|---|---|---|---|
| 3,157,179 | 11/1964 | Paullus et al. | 128/200.23 |
| 3,187,748 | 6/1965 | Mitchell et al. | 128/200.23 |
| 3,456,646 | 7/1969 | Phillips et al. | 128/200.23 |
| 3,565,070 | 2/1971 | Hanson et al. | 128/200.23 |
| 3,812,854 | 5/1974 | Michaels et al. | 128/200.16 |
| 3,826,413 | 7/1974 | Warren | 222/402.13 |
| 3,861,386 | 1/1975 | Harris et al. | 128/200.16 |

(List continued on next page.)

FOREIGN PATENT DOCUMENTS

| | | |
|---|---|---|
| B-75484/91 | 7/1994 | Australia . |
| 0 232 235 A2 | 8/1987 | European Pat. Off. . |
| 0 257 956 B1 | 5/1992 | European Pat. Off. . |
| 0 546 607 | 6/1993 | European Pat. Off. . |
| 0 572 969 | 12/1993 | European Pat. Off. . |
| 2700697 | 7/1994 | France . |
| 764 682 | 9/1980 | U.S.S.R. ............................ 128/203.27 |
| 1353440 | 11/1987 | U.S.S.R. ............................ 128/200.18 |

(List continued on next page.)

OTHER PUBLICATIONS

Newman, S.P. et al., "How should a pressurized β–adrenergic bronchodilator be inhaled?", *Eur. J. Respir. Dis.* (1981) 62:3–21.

Newman, Stephen P., "Deposition and Effects of Inhalation Aerosols," Rahms i Lund Tryckeri AB, 1983, pp. 1–113.

Newman, Stephen B., "Deposition and effects of inhalation aerosols" Dept. of Thoracic Medicine, Royal Free Hospital, London NW3 2QG.

*Primary Examiner*—Aaron J. Lewis
*Attorney, Agent, or Firm*—Karl Bozicevic; Bozicevic, Field & Francis LLP

[57] ABSTRACT

Devices, packaging and methodology for creating aerosols are provided which allow for efficient and repeatable delivery of drugs to the lungs of a patient. Devices are hand-held, self-contained units which are automatically actuated at the same release point in a patient's inspiratory flow cycle. The release point is calculated by a microprocessor which receives data from a sensor making it possible to determine inspiratory flow rate and inspiratory volume. The device is loaded with a cassette comprised of an outer housing which holds a package of individual collapsible containers of pharmaceutically active drug. Actuation of the device forces drug through a porous membrane of the container which membrane has pores having a diameter in the range of about 0.25 to 6.0 microns. The porous membrane is positioned in alignment with a surface of a channel through which a patient inhales air. The flow profile of air moving through the channel is such that the flow at the surface of the channel, and thus the surface of the porous membrane is slow. The membrane is designed in a flexible manner so that when drug formulation is forced against and through the membrane the membrane protrudes outward beyond the flow boundary layer of the channel into faster moving air.

19 Claims, 5 Drawing Sheets

U.S. PATENT DOCUMENTS

| | | | |
|---|---|---|---|
| 3,948,264 | 4/1976 | Wilke et al. | 128/203.15 |
| 3,991,304 | 11/1976 | Hillsman | 600/538 |
| 4,090,642 | 5/1978 | Baker | 222/94 |
| 4,256,071 | 3/1981 | Eastman | 91/417 R |
| 4,274,403 | 6/1981 | Struve | 128/203.15 |
| 4,469,255 | 9/1984 | Hill et al. | 222/649 |
| 4,524,769 | 6/1985 | Wetterlin | 128/203.15 |
| 4,533,082 | 8/1985 | Maehara et al. | 239/102.2 |
| 4,564,748 | 1/1986 | Gupton | 219/497 |
| 4,627,432 | 12/1986 | Newell et al. | 128/203.15 |
| 4,649,911 | 3/1987 | Knight et al. | 128/200.21 |
| 4,699,136 | 10/1987 | Krauser | 128/203.22 |
| 4,832,012 | 5/1989 | Raabe et al. | 128/200.21 |
| 4,877,989 | 10/1989 | Drews et al. | 310/323 |
| 4,922,901 | 5/1990 | Brooks et al. | 128/203.26 |
| 4,963,327 | 10/1990 | Russell | 422/120 |
| 4,984,158 | 1/1991 | Hillman | 128/200.14 |
| 5,042,472 | 8/1991 | Bunin | 128/203.15 |
| 5,063,921 | 11/1991 | Howe | 128/200.14 |
| 5,152,456 | 10/1992 | Ross et al. | 239/102.2 |
| 5,156,776 | 10/1992 | Loedding et al. | 261/27 |
| 5,186,164 | 2/1993 | Raghuprasad | 128/200.14 |
| 5,201,308 | 4/1993 | Newhouse | 128/203.15 |
| 5,327,883 | 7/1994 | Williams et al. | 128/203.12 |
| 5,372,148 | 12/1994 | McCafferty | 131/194 |
| 5,383,850 | 1/1995 | Schwab et al. | 604/58 |
| 5,396,884 | 3/1995 | Bagwell et al. | 128/200.21 |
| 5,404,871 | 4/1995 | Goodman et al. | 128/200.14 |
| 5,497,944 | 3/1996 | Weston | 239/321 |
| 5,743,250 | 4/1998 | Genda et al. | 128/200.14 |

FOREIGN PATENT DOCUMENTS

| | | | |
|---|---|---|---|
| 2 255 918 | 11/1992 | United Kingdom . | |
| 2 256 805 | 12/1992 | United Kingdom . | |
| 85/00112 | 1/1985 | WIPO | 128/203.27 |
| WO 87/04354 | 7/1988 | WIPO . | |
| WO 92/07599 | 5/1992 | WIPO . | |
| WO 92/15353 | 9/1992 | WIPO . | |
| WO 93/00951 | 1/1993 | WIPO . | |
| WO 93/12823 | 7/1993 | WIPO . | |
| WO 93/17728 | 9/1993 | WIPO . | |
| WO 94/27653 | 12/1994 | WIPO . | |

DYNAMIC PARTICLE SIZE CONTROL FOR AEROSOLIZED DRUG DELIVERY

CROSS REFERENCES

This application is a continuation-in-part of our earlier filed application Ser. No. 08/313,461 filed Sep. 27, 1994, now U.S. Pat. No. 5,522,385, which application is incorporated herein by reference and to which application we claim priority under 35 USC §120.

FIELD OF THE INVENTION

This invention relates generally to the field of devices, packaging and methodology for the delivery of pharmaceutically active drugs. More specifically, the invention relates to electromechanical devices, disposable packages and methodology for the delivery of aerosolized drug formulations.

BACKGROUND OF THE INVENTION

The intrapulmonary delivery of pharmaceutically active drugs is accomplished by a number of distinct methodologies. In accordance with one method, a pharmaceutically active drug is dispersed in a low boiling point propellant (a CFC or HFA) and loaded in a pressurized canister from which the drug/propellant formulation may be released by the use of a device generally known as a metered dose inhaler (MDI). Once released, the propellant evaporates and particles of the drug are inhaled by the patient. Another method involves the use of a nebulizer which uses vibration to create a mist of fine particles from a solution or suspension of a drug which mist is inhaled through the mouth and/or nose by the patient. In yet another method dry powered drug (which may be included in packets) are inhaled. These methods are hindered by significant problems relating to patient compliance and dosing as described further below.

The use of dry powders in systems presents some unique difficulties. Firstly, the dry powders are difficult to store and can be easily contaminated with water vapors causing the powders to clump together. Systems which do not include dry powders include the drug dissolved or suspended in a liquid carrier. Although there are advantages to these systems (e.g., avoiding the clumping of powder particles) these systems are also affected by moisture in the surrounding air, i.e. humidity. Specifically, such systems may use water as the carrier, i.e. a formulation comprised of a drug and water is used to create aerosolized particles. The carrier (such as the water) present in the particles evaporates after the particles are formed. However, the rate and amount of evaporation can vary if the surrounding humidity varies. The amount of evaporation effects the particle size which effects the amount of particles which reach the lung and the particular area of the lung which the particles can reach. Several aspects of the present invention are directed at eliminating the variability in particle size due to surrounding humidity.

SUMMARY OF THE INVENTION

Devices, packaging and methodology for creating aerosols are provided which allow for efficient and repeatable delivery of drugs to the lungs of a patient. Devices are hand-held, self-contained units which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device is loaded with a cassette comprised of an outer housing which holds a package of individual collapsible containers of pharmaceutically active drug. Actuation of the device forces drug through a porous membrane of the container which membrane has pores having a diameter in the range of about 0.25 to 6.0 microns. The porous membrane is positioned in alignment with a surface of a channel through which a patient inhales air. The flow profile of air moving through the channel is such that the flow at the surface of the channel is less than the flow rate at the center of the channel. The membrane is designed so that it protruded outward at all times or made flexible so that when drug formulation is forced against and through the membrane the flexible membrane protrudes outward beyond the flow boundary layer of the channel into faster moving air. Because the membrane protrudes into the faster moving air of the channel the particles of aerosol formed are less likely to collide allowing for the formation of a fine aerosol mist with uniform particle size.

In one embodiment, after the aerosolized mist is released into the channel energy is actively added to the particles in an amount sufficient to evaporate carrier and thereby reduce particle size. The air drawn into the device is actively heated by moving the air through a heating material which material is pre-heated prior to the beginning of a patient's inhalation. The amount of energy added can be adjusted depending on factors such as the desired particle size, the amount of the carrier to be evaporated, the water vapor content of the surrounding air and the composition of the carrier.

Particle diameter size is generally about twice the diameter of the pore from which the particle is extruded. In that it is technically difficult to make pores of 2.0 microns or less in diameter the use of evaporation can reduce particle size to 3.0 microns or less even with pore sizes well above 1.5 microns. Energy may be added in an amount sufficient to evaporate all or substantially all carrier and thereby provide particles of dry powdered drug or highly concentrated drug to a patient which particles are uniform in size regardless of the surrounding humidity and smaller due to the evaporation of the carrier. Air drawn into the device by the patient may be drawn through a desiccator containing a desiccant which removes moisture from the air thereby improving evaporation efficiency when the carrier is water. Alternatively, water vapor or aerosolized water may be introduced to the channel to saturate inhaled air thereby preventing evaporation of carrier and maintaining particle size. By adding energy some or all carrier can be evaporated. Alternatively, by adding water evaporation can be prevented. Either procedure provides a desired result in that the size of the particles may be modified or maintained regardless of the surrounding humidity of the air where the device is used.

An object of the invention is to provide a container which holds drug to be aerosolized which container comprises a porous membrane which protrudes outward in a stationary state or on the application of force forming a convex surface when drug formulation is forced against and through the membrane.

Another object is to provide a method for creating an aerosol which comprises drawing air over a surface of a porous membrane in a channel and forcing formulation against the membrane so as to protrude the membrane through a flow boundary layer into faster moving air of the channel.

Another object of the invention is to provide a drug delivery device which creates aerosolized particles of a formulation comprised of drug in a carrier and adds energy to the particles in an amount sufficient to evaporate carrier and reduce total particle size.

Another object is to provide a drug delivery device which includes a desiccator for drying air in a manner so as to remove water vapor and thereby provide consistent particle sizes even when the surrounding humidity varies.

Still another object is to provide a drug delivery device which includes a mechanism for adding water vapor to inhaled air so as to saturate the air and limit or prevent evaporation of carrier.

Another object is to provide a method of drug delivery which heats the airflow into which an aerosol is released with the heating being varied based on ambient temperature and humidity thereby providing an aerosol of consistent particle size to a patient.

Another object is to provide a device for the delivery of aerosols which measures humidity via a solid state hygrometer.

A feature of the invention is that drug can be dispersed or dissolved in a liquid carrier such as water and dispersed to a patient as dry or almost dry particles.

Another feature of the invention is that the porous membrane has a convex surface or becomes convex because it is flexible and will protrude outward upon the application of force.

An advantage of the invention is that particles do not readily agglomerate because they are released from a convex porous membrane protruding into faster moving air drawn through a channel by a patient.

Another advantage of the invention is that particle size can be adjusted by adjusting the amount of energy added and thus the amount of evaporation obtained.

Another advantage is that the size of the particles delivered will be independent of the surrounding humidity.

These and other objects, advantages and features of the present invention will become apparent to those persons skilled in the art upon reading the present disclosure and reviewing the figures forming a part hereof.

DETAILED DESCRIPTION OF PREFERRED EMBODIMENTS

Figure 1:
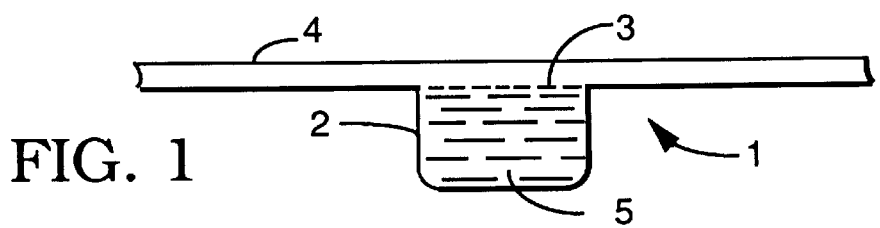
FIG. 1 is a cross-sectional view of a container of the invention.

Before the container, device and methodology of the present invention is described, it is to be understood that this invention is not limited to the particular containers, devices, systems, components, formulations and methods described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations reference to "an energy generating component" includes reference to several components and their equivalents and reference to "the method of treatment" includes reference to equivalent steps and methods known to those skilled in the art, and so forth. Although the invention is at times described in connection with specific drugs and formulations it may be used to deliver a wide range of drugs and formulations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "velocity of the drug" or "velocity of particles" shall mean the average speed of particles of formulation moving from a release point such as a porous membrane or a valve to a patient's mouth.

The term "bulk flow rate" shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "dosing event" shall be interpreted to mean the administration of a pharmaceutically active drug to a patient in need thereof by the intrapulmonary route of administration which event involves the release of drug into the inspiratory flow path of a patient. Accordingly, a dosing event may include the release of drug contained within one or more containers. A dosing event is not interrupted by a monitoring event which would indicate, if followed by further drug delivery, the beginning of a new dosing event.

The term "carrier" shall mean a liquid, flowable, pharmaceutically acceptable excipient material which a drug is suspended in or more preferably dissolved in. Useful carriers do not adversely interact with the drug and have properties which allow for the formation of aerosolized particles preferably particles having a diameter in the range of 0.5 to 12.0 microns when a formulation comprising the carrier is forced through pores having a diameter of 0.25 to 6.0 microns. Preferred carriers include water, ethanol and mixtures thereof. Other carriers can be used provided that they can be formulated to create a suitable aerosol and do not adversely effect the drug or human lung tissue.

The term "measuring" describes an event whereby either the inspiratory flow rate or inspiratory volume of the patient is measured in order to determine an optimal point in the inspiratory cycle at which to release aerosolized drug. An actual measurement of both rate and volume may be made or the rate can be directly measured and the volume calculated based on the measured rate. It is also preferable to continue measuring inspiratory flow during and after any drug delivery and to record inspiratory flow rate and volume before, during and after the release of drug. Such reading makes it possible to determine if drug was properly delivered to the patient.

The term "monitoring" event shall mean measuring lung functions such as inspiratory flow rate, and/or inspiratory volume so that a patient's lung function as defined herein, can be evaluated before and/or after drug delivery thereby making it possible to evaluate the efficiency of any treatment.

The term "inspiratory flow rate" shall mean a value of air flow calculated based on the speed of the air passing a given point in a measuring device. Measurements are preferably carried out at atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data. Measurements are preferably carried out at atmospheric pressure, ±5% and temperature in the range of about 10° C. to about 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of drug is based, in part, on a point within the inspiratory cycle likely to result in the maximum delivery of drug and based, in part, on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergics which include bronchodilators including albuterol, isoproterenol sulfate, metaproterenol sulfate, terbutaline sulfate, pirbuterol acetate, salmeterol xinotoate, formotorol; steroids including beclomethasone dipropionate, flunisolide, fluticasone, budesonide and triamcinolone acetonide. Anti-inflammatory drugs used in connection with the treatment of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. The present invention is intended to encompass the free acids, free bases, salts, amines and various hydrate forms including semi-hydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components which have a significant effect on the overall formulation such as preservatives. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

The term "drug" shall include "respiratory drug" as well as other types of drugs such as systemically effective drugs. The term is intended to encompass the presently available pharmaceutically active drugs used therapeutically and to further encompass to be developed therapeutically effective drugs which can be administered by the intrapulmonary route.

The term "therapeutic index" refers to the therapeutic index of a drug defined as $LD_{50}/ED_{50}$. The $LD_{50}$ (lethal dose, 50%) is defined as the dose of a drug which kills 50% of the animals tested, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active drug with a pharmaceutically acceptable carrier in flowable liquid form having properties such that it can be aerosolized to particles having a diameter of 0.5 to 12.0 microns. Such formulations are preferably solutions, e.g. aqueous solutions, ethanolic solutions, aqueous/ethanolic solutions, saline solutions and colloidal suspensions. Formulations can be solutions or suspensions of drug in a low boiling point propellant. Preferred formulations are drug(s) dissolved in water.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Quantitative determination of pulmonary function is important because lung disease is typically associated with deteriorating pulmonary function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "substantially dry" shall mean that particles of formulation include an amount of carrier (e.g. water or ethanol) which is equal to (in weight) or less than the amount of drug in the particle.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease is understood to be "treated" if lung function is improved even if the improvement is temporary.

The terms "aerosolized particles" and "aerosolized particles of formulation" shall mean particles of formulation comprised of pharmaceutically active drug and carrier which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Preferably, the particles have a size in the range of 0.5 micron to about 12 microns having been created by being forced through the pores of a flexible porous membrane which pores have a diameter in the range of about 0.25 micron to about 6.0 microns—the pores being present on the membrane in an amount of about ten to 10,000 pores over an area in size of from about 1 sq. millimeter to about 1 sq. centimeter.

Factors Effecting Drug Delivery

Improved repeatability and efficiency of aerosolized drug delivery is obtained by simultaneously taking into consideration a number of factors. One should adjust:

(1) the release point within a patient's inspiratory flow rate inside a range of about 0.10 to about 2.0 liters/second preferably about 0.2 to about 1.8 liters per sec. and more preferably 0.15 to 1.7 liters per sec;

(2) the release point within a patient's inspiratory volume of about 0.15 to about 2.0 liters preferably 0.15 to 0.8 liters and more preferably 0.15 to about 0.4 liters;

(3) particle size for systemic delivery in a range of about 0.5 to 6 microns and more preferably 0.5 to about 3 microns and for pulmonary delivery 0.5 to 12 microns, preferably 2.0 to 7.0 microns; more preferably 2.0 to 5.0 microns;

(4) the concentration of the drug in the carrier in the range of from about 0.01% to about 12.5% ;

(5) the amount of heat added to the air about 20 Joules to about 100 Joules and preferably 20 Joules to about 50 Joules per 10 $\mu l$ of formulation;

(6) the relative volume of air added by patient inhalation per 10 $\mu l$ of formulation at about 100 ml to 2 l and preferably about 200 ml to 1 liter for evaporation and without evaporation 50–750 ml preferably 200–400 ml;

(7) the rate of vibration of the porous membrane from 575 to 17,000 kilohertz;

(8) pore size to a range of about 0.25 to about 6.0 microns in diameter preferably 0.5 to 3 microns and more preferably 1–2 microns;

(9) viscosity of the formulation to a range of from about 25% to 1,000% of the viscosity of water;

(10) extrusion pressure in a range of about 50 to 600 psi and preferably 100 to 500 psi;

(11) ambient temperature to 15° C. to 30° C. and ambient pressure between 1 atmosphere and 75% of 1 atmosphere;

(12) the ratio of liquid carriers to each other to be consistent;

(13) the solubility of drug to carrier to use highly soluble drugs;

(14) the desiccator to maximize removal of water vapor from air;

(15) the shape of the pore opening to be circular in diameter and a conical in cross-section with the ratio of the diameter of the small to large end of the cone being about ½ to ⅒, and the shape of the porous membrane to an elongated oval;

(16) the thickness of the membrane to 5 to 200 microns; preferably 10–50 microns;

(17) the membrane to have a convex shape or to be flexible so that it protrudes outward in a convex shape beyond the flow boundary layer when formulation is forced through it. and

(18) the firing point to be at substantially the same point at each release for the parameters (1–17), i.e., each release of drug is at substantially the same point so as to obtain repeatability of dosing.

Drug Delivery with Disposable Container

FIG. 1 is a cross-sectional view of a container 1 of the invention which is shaped by a collapsible wall 2. The container 1 has an opening covered by a flexible porous membrane 3 which is covered by a removable layer 4. The membrane 3 may be rigid and protrude upward in a convex configuration away from the formulation 5. When the layer 4 is removed the wall 2 can be collapsed thereby forcing the formulation 5 against the flexible porous membrane 3 which will then protrude outward in a convex shape.

Figure 2:
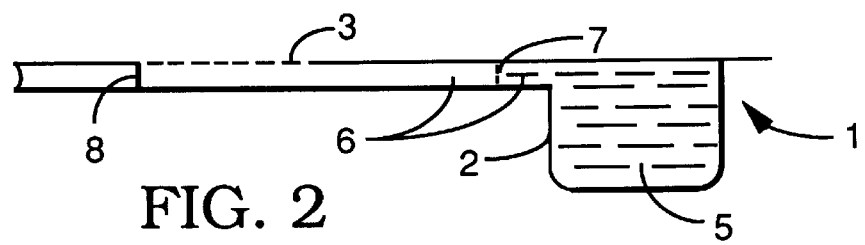
FIG. 2 is a cross-sectional view of a preferred embodiment of a container of the invention.

FIG. 2 is a cross-sectional view of a more preferred embodiment of a container 1 of the invention. The container is shaped by a collapsible wall 2. The container 1 includes an opening which leads to an open channel 6 which channel 6 includes an abutment 7 which is broken upon the application of force created by formulation 5 being forced from the container. When the abutment 7 is broken the formulation 5 flows to an area adjacent to the flexible porous membrane 3 and is prevented from flowing further in the channel 6 by a non-breakable abutment 8.

Figure 3:
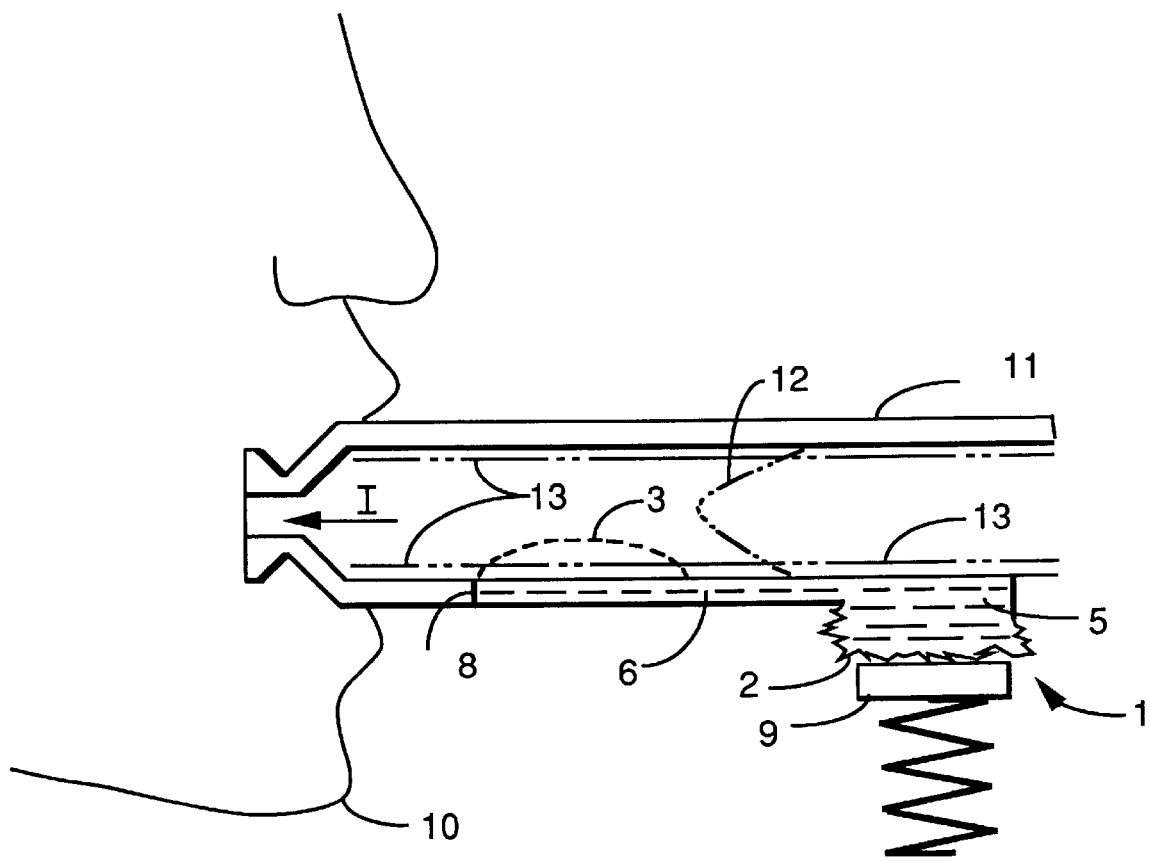
FIG. 3 is a cross-sectional view of the container of FIG. 2 in use in a channel of a drug delivery device.

FIG. 3 is a cross-sectional view of the container 1 of FIG. 2 in use. The wall 2 is being crushed by a mechanical component such as the piston 9 shown in FIG. 3. The piston may be driven by a spring, compressed gas, or a motor connected to gears which translate the electric motor's circle motion to linear motion. The formulation 5 is forced into the open channel 6 (breaking the abutment 7 shown in FIG. 2) and against and through the membrane 3 causing the membrane 3 to protrude outward into a convex configuration as shown in FIG. 3.

The piston 9 has been forced against the container wall 2 after a patient 10 begins inhalation in the direction of the arrow "I". The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity right next to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate i.e., 50% or less than the bulk flow rate.

To allow air to flow freely through the channel 11 the upper surface of the flexible porous membrane 3 is substantially flush with (i.e., in substantially the same plane as) the inner surface of the channel 11. Thus, if the membrane 3 remained in place when the formulation 5 move through the pores the formulation would be released into the slow moving or substantially "dead air" below the boundary layer 13. However, the membrane 3 protrudes outward through the boundary layer 13 into the faster moving air. This is desirable in that it aids in avoiding the agglomulation of particles. More specifically, when formulation exits the pores the formulation naturally forms spherical particles. Those particles slow down due to the frictional resistance created by the air through which the particles must travel. The particles existing behind them can face reduced air friction because the preceding particle have moved the air aside. Thus later released particles catch up with and merge into the earlier released particles. This can cause a chain reaction resulting in the formation of large particles which can not be readily inhaled into the lung—e.g., the formation of particles having a diameter of more than about 12.0 microns.

Figure 4:
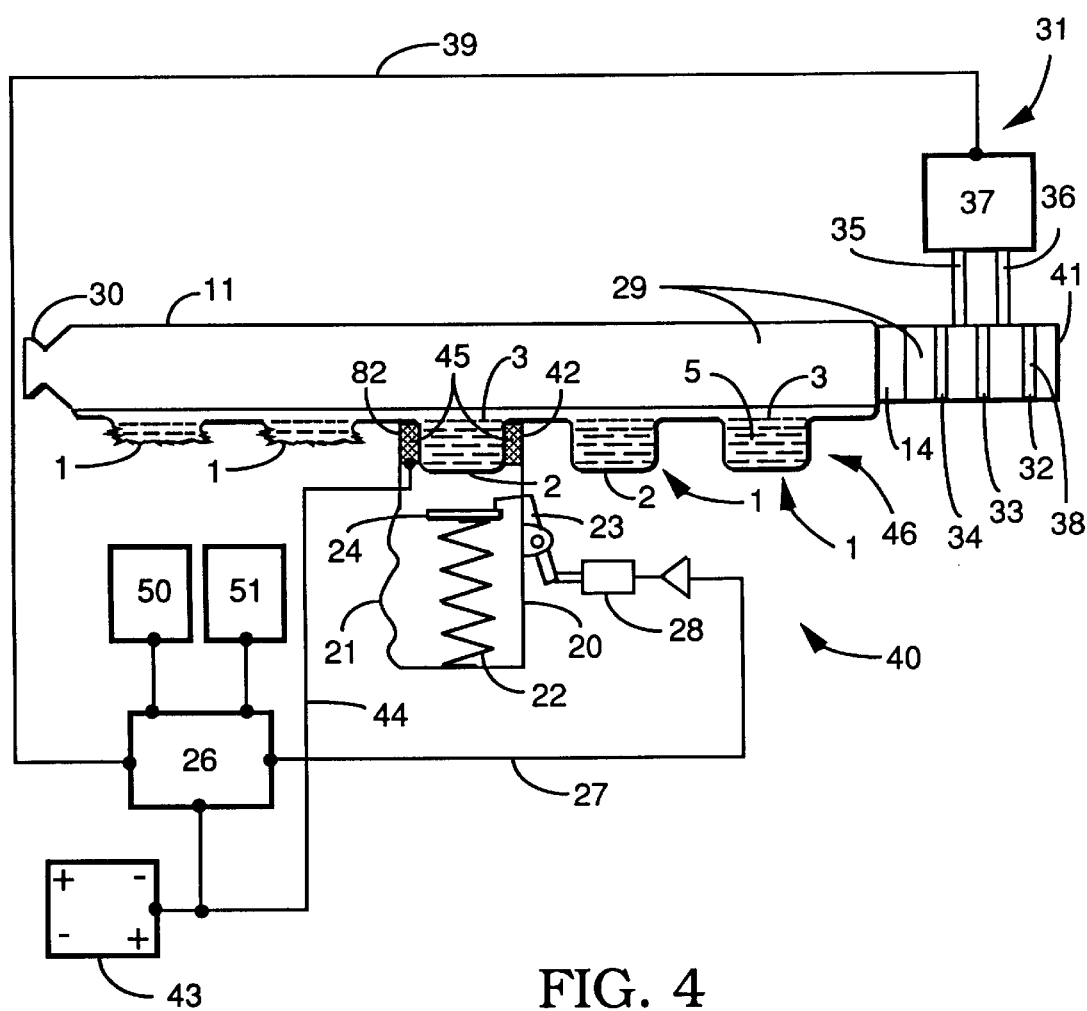
FIG. 4 is a plan view of a drug delivery device of the invention.

A plan view of a simple embodiment of a drug delivery device 40 of the present invention is shown within FIG. 4. The device 40 is loaded and operates with a plurality of interconnected disposable containers 1 which form a package 46. Before describing the details of the individual components of the device 40, a general description of the device and its operation is in order.

Conventional metered dose inhalers and nebulizers suffer from a number of disadvantages. These disadvantages result in the inability to use these devices to repeatedly deliver the same amount of drug to a patient. The disadvantages are due, in part, to the inability to control particle size—especially when the device is used in diverse environments with greatly different humidity conditions or when differing amounts of drug are delivered into a fixed amount of air or similar quantities of drug are delivered into differing amounts of air. By adding sufficient energy to the particles to evaporate any carrier particle size is reduced to a uniform minimum and any humidity variations do not affect particle variability. Further the drug dispensing device of the present invention preferably includes electronic and/or mechanical components which eliminate direct user actuation of drug release. More specifically, the device preferably includes a means for measuring inspiratory flow rate and inspiratory volume and sending an electrical signal as a result of the simultaneous measurement of both (so that drug can be released at the same point each time) and also preferably includes a microprocessor which is programmed to receive, process, analyze and store the electrical signal of the means for measuring flow and upon receipt of signal values within appropriate limits sending an actuation signal to the mechanical means which causes drug to be extruded from the pores of the porous membrane.

The device 40 shown in FIG. 4 is loaded with a disposable package 46. To use the device 40 a patient (see FIG. 3) inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a drug formulation 5 and is covered by the porous membrane 3. An air-heating mechanism 14 located in the flow path 29. The air heating mechanism 14 is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after drug delivery to conserve power.

The device 40 is a hand-held, portable device which is comprised of (a) a device for holding a disposable package with at least one but preferably a number of drug containers, and (b) a mechanical mechanism for forcing the contents of a container (on the package) through a porous membrane. The device preferably further includes (c) a heating mechanism for adding energy to the air flow into which particles are released, (d) a monitor for analyzing the inspiratory flow of a patient, (e) a switch for automatically releasing or firing the mechanical means after the inspiratory flow rate and/or volume reaches a predetermined point (f) a means for measuring ambient temperature and humidity and (g) a source of power e.g., conventional batteries.

The device for holding the disposable package may be nothing more than a narrow opening created between two outwardly extending bars 42 and 82 or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) is programmed via the microprocessor 26 to rotate the rollers only enough to move the package 39 from one container 1 to the next. In order to use the device 40, the device 40 must be "loaded," i.e. connected to a package 39 which includes drug dosage units having liquid, flowable formulations of pharmaceutically active drug therein. The entire device 40 is self-contained, light weight (less than 1 kg preferably less than 0.5 kg loaded) and portable. The power source 43 is preferably in the form of standard alkaline batteries. Two 9 volt batteries could supply the heat required to heat the air which contacts the particles by about 20° C. for about 100 doses (see FIGS. 5 and 6 re energy required).

The formulation is preferably heated after the formulation has been forced through the pores of the membrane 3 and aerosolized i.e., energy is preferably added by heating the surrounding air by means of the air-heating mechanism 14 positioned anywhere within the flow path 29. The amount of energy added by the formulation heating mechanism 45 or air-heating mechanism 5 is controlled by the microprocessor 26 based on the amount of formulation in the container 1 and other factors such as the concentration of the drug and surrounding humidity. A hygrometer 50 and thermometer 51 are electrically connected to the microprocessor 26 allowing the amount of heat to be added to be adjusted based on ambient humidity and temperature.

Potent drugs which are highly soluble in water, ethanol and/or mixtures thereof are particularly useful with the present invention in that such drugs can be used in small amounts in high concentration and thus require less energy to obtain evaporation of the carrier. For example, a prescribed dose of Fentanyl (a highly potent narcotic) is 100 micrograms and such can be dissolved in 10 microliters of water. Particles having a diameter of 6.3 microns can be formed and subjected to evaporation to obtain a particle of one micron in diameter. In the respiratory track this one micron particle would be expected to grow to a 3 micron particle due to moisture added from the high humidity environment of the respiratory tract.

Figure 5:
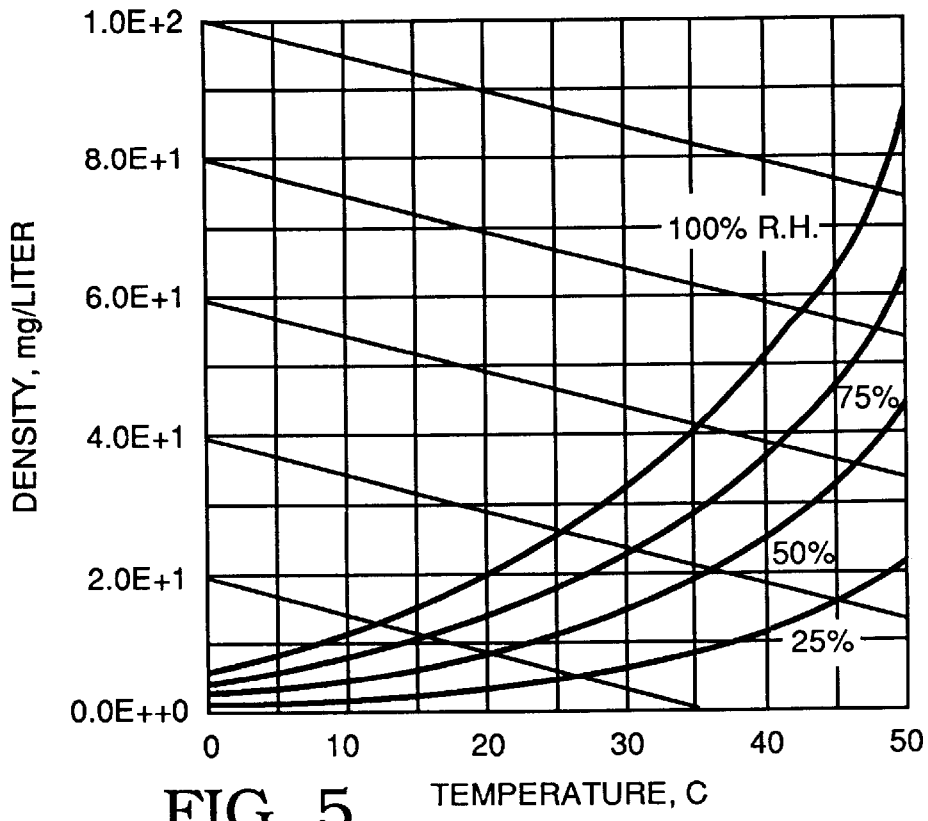
FIG. 5 is a graph plotting the density of water vapor in air versus temperature.

FIG. 5 is a graph which can be used in calculating the amount of energy needed to control the size of delivered droplets by controlling the amount of evaporation of carrier from the aerosolized droplets. The graph of FIG. 5 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. These values imply that a liter of air will cool 2 celsius degrees for every milligram of water evaporated, i.e. evaporating 10 micro-liters will cool a liter of air 20 celsius degrees.

FIG. 5 can be used to calculate the amount of preheating needed to evaporate all or substantially all of the carrier in the aerosolized particles. As an example, assume the initial ambient conditions are 25° C. and 50% relative humidity. Further, assume that one wants to evaporate 10 μl (10 mgs) of water from an aqueous drug solution. Finally, assume the final relative humidity is 75%. Under these conditions the aqueous carrier would not evaporate completely. More specifically, the final particles would contain approximately equal amounts of drug and water. To calculate the amount of energy to add for this delivery manoeuver, refer to FIG. 5. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation.

Figure 6:
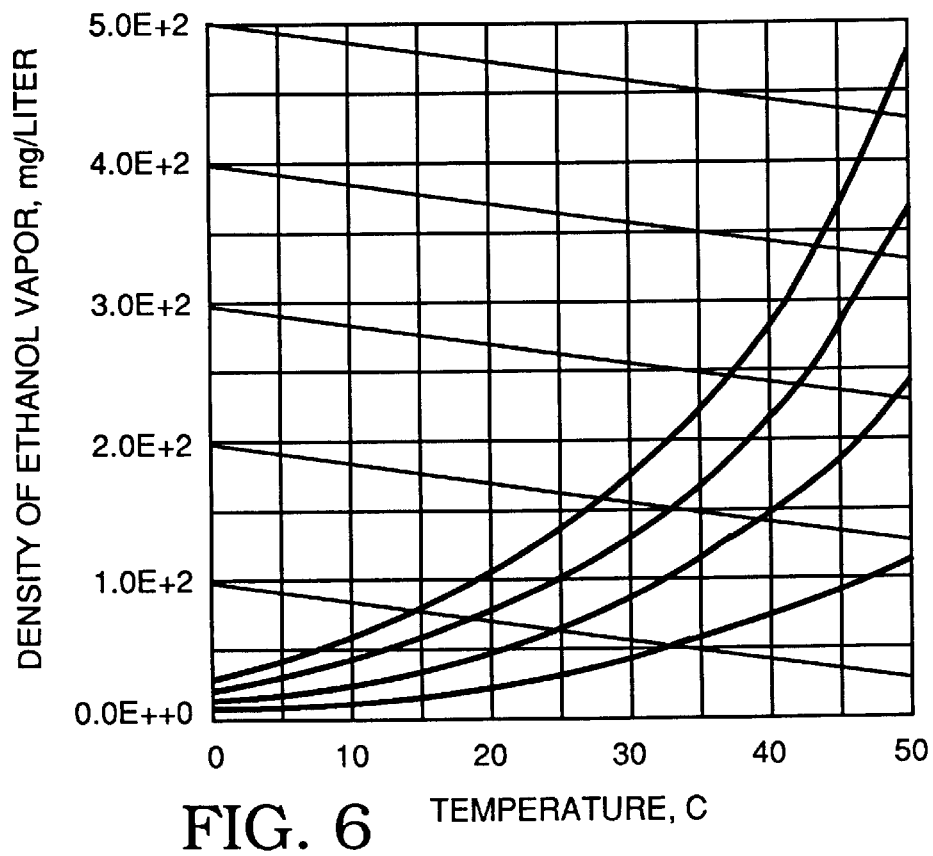
FIG. 6 is a graph plotting the density of ethanol vapor in air versus temperature.

FIG. 6 includes similar information with respect to ethanol which can be used in a similar manner. FIG. 5 shows the density of water vapor in air at 25, 50 and 75° C. and 100% saturation with the air mass trajectory during evaporation also shown. The same is shown in FIG. 6 for the density of ethanol in air.

The evaporation and growth rates of aqueous droplets is a function of their initial diameter, the amount of drug dissolved therein (concentration) and the ambient relative humidity. The determining factor is whether the water vapor concentration at the surface of the droplet is higher or lower than that of the surrounding air. Because the relative humidity at the surface of a particle (i.e. droplet of aerosolized formulation) is close to 100% for all the high concentration formulations, a five micron droplet will evaporate to a 1 micron dry particle in 0% humidity in less than 20 ms. However, if a particle of drug 1 micron diameter is inhaled into the lungs (99.5% humidity) it will grow to about 3 microns in diameter in approximately one second by accumulating water from the humid lung environment.

The opening 38 may have a desiccator 41 positioned therein which desiccator includes a material which removes water vapor from air being drawn into the flow path 29. By reducing or more preferably eliminating water vapor from the air any water in particles of formulation can be more efficiently evaporated. Further, the particles delivered to the patient will have a smaller and more uniform size even if energy is not added to cause evaporation of water from the particles of the formulation.

The device may include a mouth piece 30 at the end of the flow path 29. The patient inhales from the mouth piece 30 which causes an inspiratory flow to be measured by flow sensor 31 within the flow path which path may be, and preferably is, in a non-linear flow-pressure relationship. This inspiratory flow causes an air flow transducer 37 to generate a signal. This signal is conveyed to a microprocessor which is able to convert, continuously, the signal from the transducer 37 in the inspiratory flow path 29 to a flow rate in liters per minute. The microprocessor 26 can further integrate this continuous air flow rate signal into a representation of cumulative inspiratory volume. At an appropriate point in the inspiratory cycle, the microprocessor can send a signal to send power from the power source 43 to the air-heating mechanism 14 which uses information from the hygrometer 50, thermometer 51 and particle size and amount of formulation. The microprocessor also sends a signal to an actuator which causes the mechanical means (e.g., the piston 24) to force drug from a container of the package into the inspiratory flow path 29 of the device and ultimately into the patient's lungs. After being released, the drug and carrier will pass through a porous membrane 3 to aerosolize the formulation and thereafter enter the lungs of the patient.

Figure 8:
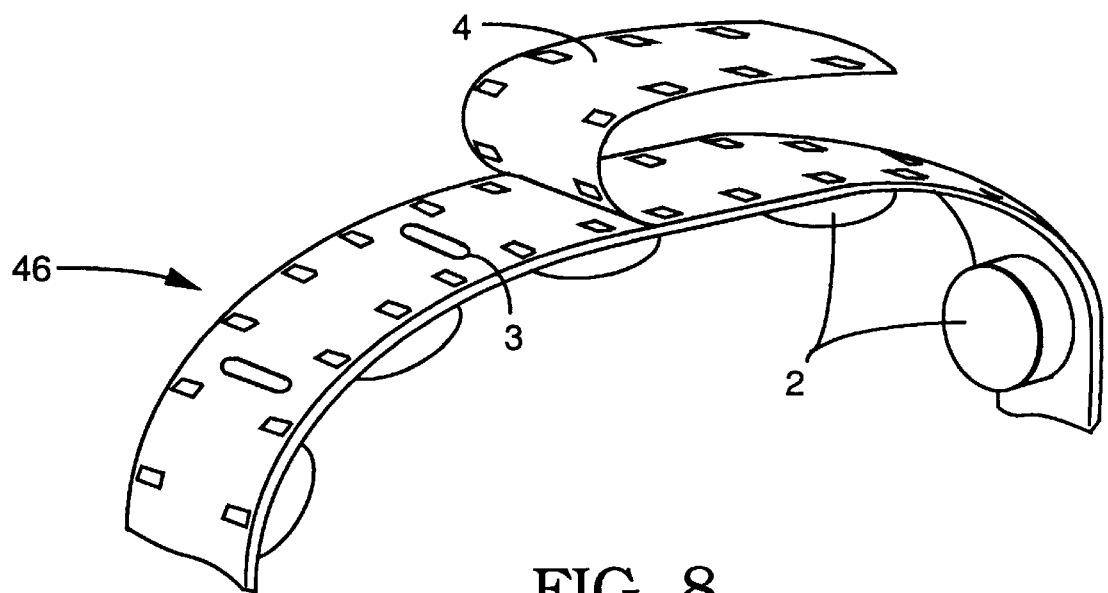
FIG. 8 is a perspective view of the package of the invention.
Figure 9:
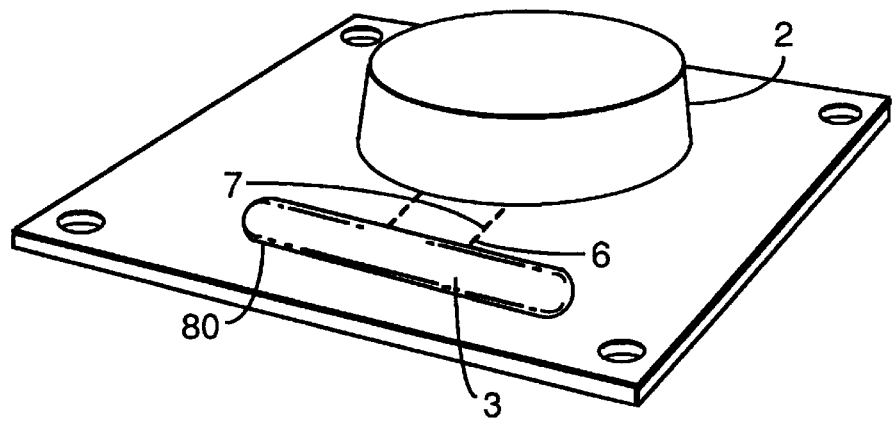
FIG. 9 is a perspective view of a container of the invention.

The convex shape of the membrane 3 plays an important role at this point. The membrane may be rigid and convex and a rigid convex membrane 80 is shown in FIG. 9. Alternatively, formulation 5 is forced from the container 1 by force applied from a source such as the piston or plate 24 causing the formulation 5 to press against a flexible membrane 3 causing it to convex outward beyond the plan of the resting surface of the membrane 3 and beyond the plan of the inner surface of the channel 11 which is aligned with the surface or membrane 3 when the container 1 is in a drug release position. The convex shape of the membrane 3 is shown in FIG. 3. The convex upward distortion of the membrane is important because it positions the pores of the membrane beyond the boundary layer 13 (shown in FIG. 3) into faster moving air of the channel 29. A number of containers may be connected together to form a package 46 as is shown in FIG. 8. The package 8 is in the form of an elongated tape but can be in any configuration, e.g., circular, square, rectangular, etc.

When pores of the membrane 3 are positioned beyond the boundary layer into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung; and (b) result in an aerosol with diverse and unpredictable particle sizes. Either or both (a) and (b) can result in erratic dosing.

The air-heating mechanism 14 heats the surrounding air within the flow path 29. This causes carrier in the formulation to be evaporated more readily. If sufficient heat is added the only material reaching the patient is the substantially dry powder drug.

The methodology of the present invention could be carried out with a device that obtains power from a plug-in source. However, the device is preferably a self-contained, hand-held device which is battery powered. Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

When the formulation 5 includes water as all or part of the carrier it is also desirable to include a desiccator 41 within the flow path 29. The desiccator 41 is preferably located at the initial opening 38 but maybe located elsewhere in the flow path 29 prior to a point in the flow path when the formulation is fired into the flow path in the form of aerosolized particles. By drawing air through the desiccator 41 water vapor within the air is removed in part or completely. Therefore, only dried air is drawn into the remainder of a flow path. Since the air is completely dried water carrier within the aerosolized particles will more readily evaporate. This decreases the energy needs with respect to the heating devices 14. The desiccator material can be any compound which absorbs water vapor from air. For example, it may be a compound selected from the group consisting of $P_2O_5$, $Mg(ClO_4)$, KOH, $H_2SO_4$, NaOH, CaO, $CaCl_2$, $ZnCl_2$, and $CaSO_4$.

It is important to note that the firing threshold of the device is preferably not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of reproducibly delivering the same amount of drug to the patient with each release of drug.

The device preferably includes a means for recording a characterization of the inspiratory flow profile for the patient which is possible by including a microprocessor 26 in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

FIG. 4 shows a cross-sectional plan view of a hand held, self-contained, portable, breath-actuated inhaler device 40 of the present invention. The device 40 is shown with a holder 20 having cylindrical side walls and a hand grip 21. The holder 20 is "loaded" in that it includes a container 1. A plurality of containers 1 (2 or more) are preferably linked together to form a package 46.

The embodiment shown in FIG. 4 is a simple version of the invention. The device 40 may be manually actuated and loaded. More specifically, the spring 22 may be compressed by the user until it is forced down below the actuation mechanism 23. When the user pushes the actuation mechanism 23 the spring 22 is released and the mechanical means in the form of a plate 24 is forced upward against a wall 2 of a container 1. When the container 1 is compressed its contents are forced out through the membrane 3 and aerosolized. Two additional containers 1 shown to the left is unused. The device of FIG. 4 would not require the use of low boiling point propellants such as low boiling point fluorocarbons. Numerous additional features and advantages of the present invention can be obtained by utilizing the monitoring and electronic components described below.

It is important to note that a variety of devices can be used in order to carry out the methodology (including the respiratory disease treatment methodology) of the present invention. However, the device must be capable of aerosolizing drug formulation in a container and preferably does such forcing formulation through a porous membrane with the release point based on pre-programmed criteria which may be mechanically set or electronically set via criteria readable by the microprocessor 26. The details of the microprocessor 26 and the details of other drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration" which patent is incorporated in its entirety herein by reference, and it is specifically incorporated in order to describe and disclose the microprocessor and program technology used therewith. The use of such a microprocessor with a drug delivery device is disclosed in our earlier filed U.S. application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different drugs for different types of treatment.

Microprocessor 26 sends signals via electrical connection 27 to electrical actuation device 28 which actuates the means 23 which fires the mechanical plate 24 forcing drug formulation in a container 1 to be aerosolized so that an amount of aerosolized drug is delivered into the inspiratory flow path 29 when the flexible membrane 3 protrudes outward through the flow boundary layer. A signal is also sent to the heater 14 to add heat energy to the air in the flow path 29. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 1. The recorded information can be read later by the care-giver to determine the effectiveness of the treatment. In order to allow for ease of use, it is possible to surround the inspiratory flow path 29 with a mouth piece 30.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. The flow sensor 31 includes screens 32, 33 and 34 which are positioned approximately b ¼" apart from each other but may be comprised of a single screen or include a non-linear flow path. It is preferable to include the desiccator 41 at a point prior to the screens 32, 33 and 34 in the flow path so that the elimination of water vapor is considered in any measurement.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 1 so that a controlled amount of respiratory drug is delivered to the patient. The microprocessor 26 is optionally connected to an optionally present vibrating device 45 which may be activated.

Vibration Device

The vibration device 45 creates ultrasonic vibrations which are preferably at right angles to the plane of the membrane 3. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 3 allowing for maximum use of the energy towards aerosolizing the liquid formulation 5. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the membrane (generally comprised of a polymeric plastic-like material) used for producing the drug dosage unit and/or the efficiency of the connection.

Vibration is applied while the formulation 5 is being forced from the pores of the polycarbonate membrane 3. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about 50 to 600 psi, preferably 100 to 500 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the porous membrane with a relatively low pressure e.g., pressure less than 500 psi in that lower pressure reduces the chance of breaking the membrane during the release of formulation and makes it possible to make a thinner membrane. The thinner membranes make it easier to make small holes in that the holes or pores of the membrane are created using a focussed LASER. It is possible to reduce the pressure further by making the holes conical in cross-section. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:10 i.e., the larger opening is between 2 and 10 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferable less than 350 psi.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane 3 prevent collisions. Specifically, the patient inhales thereby creating an air flow toward the patient over the protruding membrane 3. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 3 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid membrane 80 as shown in FIG. 8. Using such a configuration makes it possible to better utilize the air flow relative to all of the particles of formulation being forced form the pores of the membrane 3. When a circular opening is used, particles which are towards the center of the circle may not be carried along by the air being drawn over the membrane 3 and will collide with each other. The elongated rectangle could be formed in a circle, thereby providing an annular opening and air could be forced outward from the outer and inner edges of the circle formed. Further details regarding such are described in U.S. patent application Ser. No. 08/247,012, filed May 20, 1994 which is incorporated herein by reference to disclose and describe such.

Operation of the Device 40

The device of FIG. 4 shows all of the components present within the single, hand-held, portable breath actuated device, e.g. the microprocessor 26 and flow sensor 31 used to provide the electronic breath actuated release of drug. The device of FIG. 4 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, and out of the membrane 3 into the flow path 29 where the air surrounding the particles is optionally heated by the air heater 14. Further details regarding microprocessors 26 of FIG. 4 are described within U.S. Pat. No. 5,394,866, issued Mar. 7, 1995, entitled "An Automatic Aerosol Medication Delivery System and Methods", which is incorporated herein by reference in its entirety and specifically incorporated in order to describe and disclose flow measurements, the microprocessor and program technology used therewith.

Microprocessor 26 of FIG. 4 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of respiratory drug to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 $\mu$g of a given respiratory drug per day when the patient is normally dosed with approximately 100 $\mu$g of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 $\mu$g of respiratory drug is given in a given 15-minute period over which the patient will make approximately 10 inhalations with 1 $\mu$g of drug being delivered with each inhalation. By providing this feature, greater assurances are obtained with respect to delivering the respiratory drug gradually over time and thereby providing relief from the symptoms of respiratory disease without overdosing the patient.

The microprocessor 26 of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor 26 of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

Method of Administration

The method and device of the invention provides a number of features which make it possible to achieve the controlled and repeatable dosing procedure required for the treatment of diseases, particularly diseases treated with drugs with a low therapeutic index, e.g., drugs such as insulin (which is potent) to treat diabetes (which is life threatening). First, the membrane is permanently convex or is flexible and protrudes into fast moving air aiding the elimination of particle collisions. Second, the invention makes it possible to eliminate any carrier from the aerosolized particles and provide dry drug particles to a patient which particles can be manufactured to have a uniform size. By delivering particles of uniform size repeatability of dosing is enhanced regardless of the surrounding environment, e.g. different humidity conditions. Third, the device makes it possible to administer drug at the same point with respect to inspiratory flow rate and inspiratory volume at each drug delivery point thereby improving repeatability of dosing.

The method of the invention involves the release of a liquid, flowable drug from individual disposable containers which may be interconnected in a package. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. The membrane of the container is also disposable thereby preventing clogging of pores which takes place with reuse. The invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides potential environmental benefits and would be particularly useful if government regulations prevented further use of devices which dispensed low boiling point fluorocarbons.

In addition to environmental advantages, the present invention offers advantages due to the relatively slow speed at which the aerosol dispersion is delivered to the patient. A conventional metered dose inhaler device discharges the aerosol outward at a relatively high rate of speed which causes a large amount of the aerosol particles to make contact with the inside of the patient's mouth and the back of the patient's throat. This decreases the amount of drug actually administered to the patient's lungs as compared with the present system, wherein the aerosol is delivered at a relatively slow rate of speed and can be inhaled slowly by the patient.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which fires a mechanical means (and activates the vibration device) which causes drug to be forced out of the container and aerosolized. Accordingly, drug is repeatedly delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the most important feature. A more important feature is the reproducibility of the release of a tightly controlled amount of drug (with a narrow range of particle size) repeatedly at the same particular point in the respiratory cycle so as to assure the delivery of a controlled and repeatable amount of drug to the lungs of each individual patient, i.e. intrapulmonary drug delivery with tightly controlled dosing.

Plasma Concentrations Obtained

Figure 7:
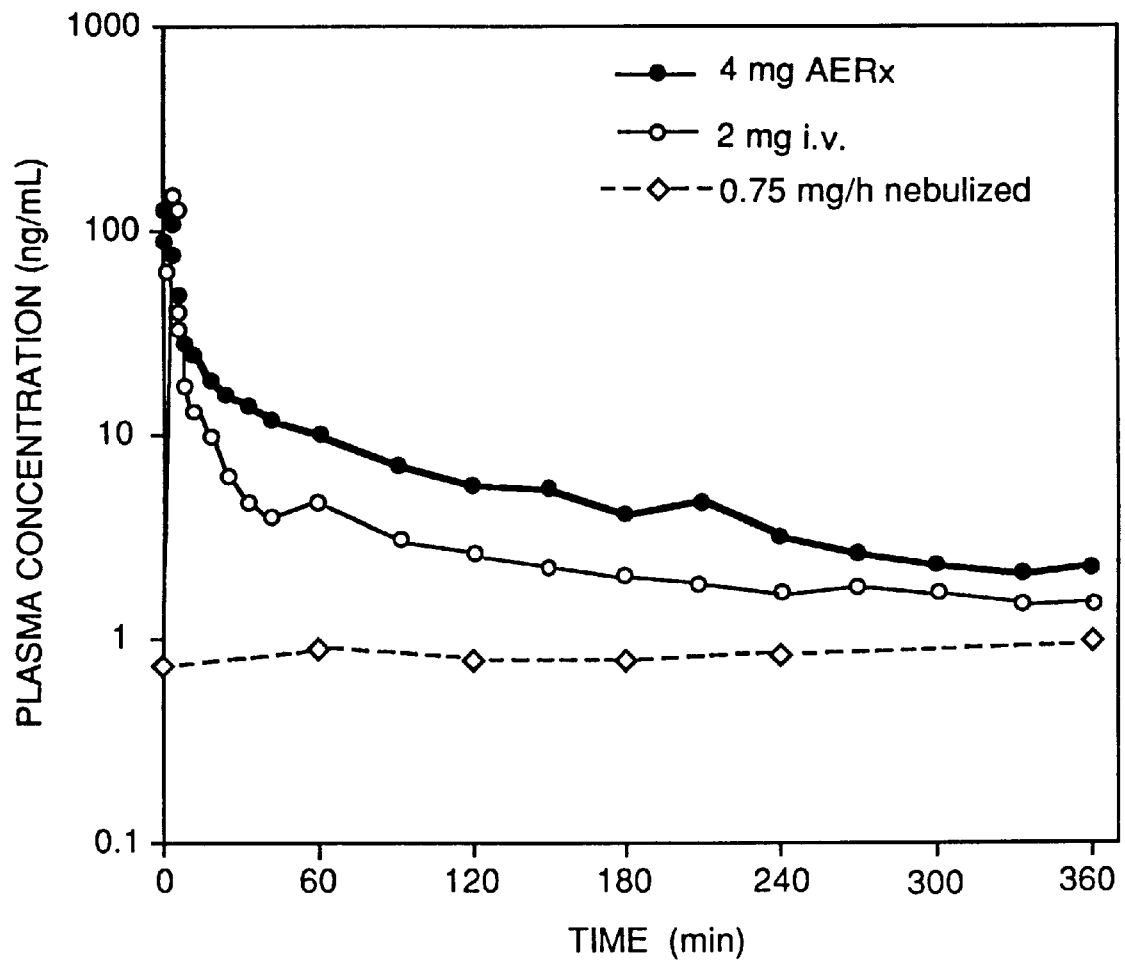
FIG. 7 is a graph plotting time versus plasma concentration for morphine administered (a) I.V., (b) via the invention and (c) via a nebulizer.

FIG. 7 is a graph plotting the plasma concentration of morphine over time for morphine administered by three different routes. Specifically, as shown within the graph the plasma concentration is plotted over time for delivery via intravenous administration, the "AERX" system of the present invention and a nebulizer. Different amounts are administered with the three different systems. However, it can be seen that the administration of 4 milligrams using the present invention very closely tracks the administration of 2 milligrams I.V in terms of the plasma concentration obtained as measured in nanograms per milliliter. Thus, FIG. 7 shows that the present invention provides very high degree of efficiency with respect to the delivery of drug to a patient and that degree of efficiency can be shown to coincide very well with I.V. administration.

The heating component(s) and/or the desiccator to remove water vapors aid in providing repeatability in dosing in that the particles reaching the patient will have the same size regardless of the surrounding humidity. By keeping the particle size the same at each dosing event the particles deposit at the same general area of the lung at each event. These features improve repeatability along with automatic control of the drug release mechanism, combined with frequent monitoring events in order to calculate the optimal flow rate and time for the release of respiratory drug. Further, the particles will have uniform size in that all carrier is removed regardless of the humidity of the surrounding environment. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the point of release of the respiratory drug in a manner calculated to provide for the administration of an amount of respiratory drug to the patient presently needed by the patient at each dosing event.

When administering drug using the inhalation device of the present invention, the entire dosing event can involve the administration of anywhere from 10 μl to 1,000 ml of drug formulation, but more preferably involves the administration of approximately 50 μl to 10,000 μl of drug formulation. Very small amounts of drug (e.g., nanogram amounts) may be dissolved or dispersed within a pharmaceutically acceptable, liquid, excipient material to provide a liquid, flowable formulation which can be readily aerosolized. The container will include the formulation having drug therein in an amount of about 10 ng to 300 μg, more preferably about 50 μg. The large variation in the amounts which might be delivered are due to different drug potencies and different delivery efficiencies for different devices, formulations and patients.

The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of respiratory drug.

One of the important features and advantages of the present invention is that the microprocessor can be programmed to take a number of different criteria into consideration with respect to dosing times. For example, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 μg (or two 100 μg containers) of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 μg of a given drug during an hour which could only be released in amounts of 25 μg with each release being separated by a minimum of five minutes.

The dosing program can be designed with some flexibility. For example, if the patient normally requires 250 μg per day of respiratory drug, the microprocessor of the inhalation device can be programmed to provide a warning after 250 μg have been administered within a given day and to continue the warning thereafter to alert the user of possible overdoses. By providing a warning and not a lock-out, the device allows for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of respiratory drug released and calculate the approximate amount of respiratory drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of respiratory drug merely by the manual actuation of a button to fire a burst of respiratory drug into the air or a container.

A variety of different embodiments of the dispersion device of the invention are contemplated. In accordance with one embodiment it is necessary to carry out manual cocking of the device. This means that energy is stored such as by retracting a spring so that, for example, a piston can be positioned below the drug containing container. In a similar manner a piston connected to a spring can be withdrawn so that when it is released it will force air through the air dispersion vents. Automatic cocking of forced storing systems for both the drug formulation and the air flow may be separate or in one unit. Further, one may be manual whereas the other may be done automatically. In accordance with one embodiment the device is cocked manually but fired automatically and electronically based on monitoring the patients inspiratory flow. The formulation may be physically moved through the porous membrane in a variety of different ways. Formulation may be forced through the membrane by a piston or, without applying force to the formulation, the membrane being vibrated at frequencies sufficient to create an aerosol.

The microprocessor 26 of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer respiratory drug. In addition to indicating the time of administration (preferably by audio signal), the device can indicate the amount of respiratory drug which should be administered by providing a visual display. For example, the audio alarm could sound alerting the patient that respiratory drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of respiratory drug which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs and formulations.

Supplemental Treatment Methodology

The present invention can be used to deliver many types of drugs. Specifically, the disposable containers, packages, and drug delivery devices can be used to deliver drugs which have a systemic effect (e.g. narcotics, proteins such as insulin and antibiotics) as well as drugs which have a local effect primarily on the lungs (e.g. bronchodilators DNAse or steroids). Because the present invention allows drug delivery directly to the lungs there are certain advantages with respect to using the invention for the delivery of drugs to treat respiratory diseases. For this reason, much of the operation of the invention is described in connection with the delivery of respiratory drugs. However, the invention is not limited to respiratory drugs and the examples described herein would apply with respect to the delivery of drugs having a systemic effect. This is true also with respect to the supplemental treatment methodology described below even though this methodology is described with specific reference to respiratory diseases being treated with respiratory drugs.

Patients suffering from a given disease such as a respiratory disease may be treated solely with respiratory drug as indicated above, i.e. by intrapulmonary delivery. However, it is possible to treat such patients with a combination of intrapulmonary delivery and other means of administration such as oral administration. The oral drug is preferably given in amount so as to maintain a baseline level of drug within the circulatory system which is sufficient to maintain body functions such as lung function at an acceptable level. However, this baseline level of drug to blood ratio (or serum blood level) must be raised in order to improve the body function such as lung function during periods of stress such as respiratory difficulty such as an asthma attack and such can be accomplished by the intrapulmonary administration of a drug such as a respiratory drug using the present invention.

Based on the above, it will be understood by those skilled in the art that a plurality of different treatments and means of administration can be used to treat a single patient. For example, a patient can be simultaneously treated with respiratory drug by transdermal administration, respiratory drug via intrapulmonary administration in accordance with the present invention, and drugs which are orally administered.

The device 40 schematically shown within FIG. 4 can be specifically operated as follows. A container 1 is loaded into the device 6. The device is then armed meaning that the piston such as the spring-loaded piston 24 is cocked. If applicable another piston (not shown) used to compress the liquid formulation in a dual container system is cocked. Further, a container 1 of the package is moved into position and any cover is stripped off of the porous membrane 3. Thereafter, the patient withdraws air from the mouthpiece 30 and the patient's inhalation profile is developed using the microprocessor 26. After the inhalation profile is determined, the microprocessor calculates a point within the inhalation profile at which the drug should be released in order to maximize repeatability of the dosing, e.g. by plotting a curve of breath velocity versus time and determining the point on the curve most likely to provide repeatability of dosing. However, in order to carry out methodology in accordance with the present invention it is not necessary to plot any curve of breath velocity versus time. The device can be set so that the dose will be repeatedly released at approximately the same point with respect to inspiratory flow rate and inspiratory volume. If the device repeatedly fires at the same inspiratory flow rate and inspiratory volume each time the patient will receive substantially the same dose. Both criteria must be measured and used for firing to obtain repeatability.

Further details with respect to obtaining improved repeatability of dosing in addition to improved delivery efficiency are disclosed within related application entitled: "Intrapulmonary Drug Delivery Within Therapeutically Relevant Inspiratory Flow/Volume Values" filed on Jul. 11, 1994, U.S. Ser. No. 08/273,375 which application is incorporated herein by reference. The microprocessor of the present invention can be programmed to release drug based on all or any of the following parameters.

(1) Delivery should be at an inspiratory flow rate inside a range of about 0.10 to about 2.0 liters per second (efficiency can be obtained by delivering at a flow rate in a range of 0.2 to about 1.8 liters per second and more preferably 0.15 to 1.7 liters per second). Repeatability of the delivery is obtained by releasing at substantially the same inspiratory flow rate at each drug release.

(2) Delivery should be at a point within a patient's inspiratory volume of about 0.15 to about 2.0 liters (further efficiency of delivery can be obtained by delivering within a range of 0.15 to 0.8 liters and more preferably 0.15 to about 0.4 liters). Repeatability of delivery is obtained by delivering at the same inspiratory volume at each release of drug.

(3) Delivery is improved by providing a system which creates particles for systemic delivery wherein the particles are in the range of about 0.5 to about 12.0 microns, preferably 0.5 to 6 microns and more preferably 0.5 to about 3 microns. The size is somewhat larger for pulmonary delivery i.e., delivery to the lung surface for treatment so that the particles should in the range of 0.5 to 12 microns, preferably 2.0 to 7 microns and more preferably 2.0 to 5.0 microns.

(4) It is desirable to have obtained a concentration of the drug in the carrier in the range of from about 0.01 to about 12.5% preferably 0.1 to 10%. By maintaining the concentration of drug to carrier in this range it is possible to create particles which are somewhat larger than would be desirable for delivery but to reduce those particles in size by evaporation of carrier.

(5) Air drawn into the flow path of the aerosolized particles is heated by adding energy to each 10 $\mu$l of formulation in an amount of about 20 Joules to 100 Joules, more preferably 20 Joules to 50 Joules. The heated air aids in reducing the effect of humidity and evaporates carrier away from the particles thereby providing smaller particles for inhalation.

(6) Air is added to the aerosolized formulation by the patient drawing air into the aerosolized mist in an amount of about 100 milliliters to 2 liters per 10 microliters of aerosol formulation.

(7) Vibration may be created on the porous membrane in an amount 575 to 32,000, preferably 1,000 to 17,000 and more preferably 2,000 to 4,000 kilohertz.

(8) The pore size of the membrane is regulated within a range of 0.25 to about 6.0 microns, preferably 0.5 to 3 microns and more preferably 1 to 2 microns. This size refers to the diameter of the pore through which the formulation exits the membrane. The diameter of the opening into which the formulation flows may be 2 to 10 times that size in diameter thereby providing a conical configuration.

(9) The viscosity of the formulation affects the amount of pressure which needs to be applied to force the formulation through the pores and should be within the range of 25% to 1,000% the viscosity of water.

(10) The extrusion pressure is regulated within a range of 50 to 600 psi more preferably 100 to 500 psi. Lower pressures may be obtained by using the conical configuration for the pore size.

(11) The microprocessor should also be provided information regarding the ambient temperature and atmospheric pressure. The temperature is preferably close to room temperature i.e., within a range of 15° C. to 30° C. An atmospheric pressure is generally 1 atmosphere or slightly lower at higher altitudes, e.g., about 75% of 1 atmosphere.

(12) To provide for consistency in dosing the ratio of the carrier to drug should be maintained constant and more highly soluble drugs are more desirable. However, it is possible to use drugs that are insoluble by creating suspensions or by using solubility enhancers.

(13) A desiccator is preferably used to remove water vapor from air drawn into the flow path by the patient.

(14) The pores are preferably placed in the porous membrane in an elongated oval or elongated rectangular configuration. By configuring the pores in this manner and drawing air perpendicularly over the narrower dimension of the configuration it is possible to reduce the amount of collisions between particles and thereby avoid particles collision resulting in accumulation.

(15) The thickness of the membrane is preferably regulated in the range of 5 to 200 microns or more preferably 10 to 50 microns. Thinner membranes are useful in that less pressure is required to force formulation through the membrane. The membrane has a tensile strength of 5,000 to 20,000, preferably 8,000 to 16,000 and more preferably 14,000 to 16,000 psi.

(16) The membrane is configured so as to have a convex configuration which protrudes into faster moving air created by the patient's inhalation or is designed to be flexible so that it will assume a convex configuration when formulation is forced through the membrane.

(17) After the microprocessor is provided information with respect to above parameters or measurements a drug release point is chosen the microprocessor will continually return to substantially the same firing point at each drug delivery so as to obtain repeatability of dosing.

After drug has been delivered it is possible to discontinue any readings with respect to flow and/or volume. However, it is preferable to continue readings with respect to both criteria after drug has been released. By continuing the readings the adequacy of this patient's particular drug delivery maneuver can be determined. All of the events are recorded by the microprocessor. The recorded information can be provided to the caregiver for analysis. For example, the caregiver can determine if the patient correctly carried out the inhalation maneuver in order to correctly delivery drug and can determine if the patient's inhalation profile is effected by the drug (e.g. with respiratory drugs) in order to determine the effectiveness of the drug in treating the patient's particular condition. If necessary, various adjustments can be made such as in the type of drug or the particle size to obtain a particular desired result.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A disposable container for use in aerosolized delivery of drugs to the lungs, comprising:

a wall which is collapsible upon the application of force;

an opening in the container which opening is covered at least in part by a flexible porous membrane having pores with a diameter in the range of about 0.25 to about 6.0 microns the membrane being sufficiently flexible such that it will protrude outward in a convex configuration upon the application of force; and a formulation comprised of a pharmaceutically active drug and a carrier which formulation is characterized by its ability to form an aerosol of particles which can be inhaled into a patient's lungs when the formulation is moved through the pores of the membrane.

2. The container of claim 1, wherein the opening forms an open channel leading from the opening to a breakable seal beyond which is an area covered by the flexible porous membrane.

3. The container of claim 1, wherein the pores have a cross-sectional configuration with a small end opening of 0.25 to 6.0 microns in diameter and a large end opening of 2 to 10 times the diameter of the small end.

4. A disposable package comprising a plurality of interconnected disposable containers as claimed in claim 1.

5. A method for creating an aerosol, comprising:

drawing air through a channel and over a surface of a flexible, disposable, porous membrane having pores with a diameter in the range of about 0.25 to about 6.0 microns;

forcing a formulation comprised of a pharmaceutically active drug and a carrier through the pores of the membrane with sufficient force as to protrude the membrane outward in a convex configuration away from the formulation and toward the air drawn through the channel.

6. The method of claim 5, wherein the flexible membrane protrudes outward beyond a boundary layer of air flow created in the channel and the air is drawn over the protruded membrane to a channel end, via a substantially linear flow path.

7. The method of claim 5, further comprising:

measuring airflow through the channel and determining inspiratory flow rate and inspiratory volume; and determining a beginning point to force formulation through the pores of the membrane based on real time values of inspiratory flow rate and inspiratory volume.

8. The method of claim 7, further comprising:

repeating the drawing, measuring, determining and forcing steps in a manner such that the forcing repeatedly begins at substantially the same inspiratory flow rate and inspiratory volume wherein the forcing occurs at an inspiratory flow rate in the range of about 0.10 to about 2.0 liters/second and an inspiratory volume in the range of about 0.15 to about 1.5 liters.

9. The method of claim 7, wherein the measuring is carried out mechanically.

10. The method of claim 7, wherein the measuring is carried out electronically.

11. The method of claim 5, further comprising:

adding energy to the aerosolized particles by actively heating air brought into contact with the particles; and inhaling the particles into the lungs of a patient.

12. The method of claim 11, wherein energy is added in an amount such that 50% or more of the carrier in the particles when formed is evaporated prior to the particles reaching the patient and wherein the energy is added by actively heating air by moving air through a heated material which material is heated prior to the patient's inhalation.

13. The method of claim 11, wherein energy is added in an amount such that carrier is evaporated to the extent that the particles are substantially dry prior to the particles reaching the patient, wherein the carrier is selected from the group consisting of water, ethanol and mixtures thereof, and further wherein the porous membrane includes from 10 to 10,000 pores over an area of from about 0.1 mm$^2$ to about 1 cm$^2$.

14. A method of drug delivery, comprising:

inhaling air through a desiccator into a channel wherein the desiccator absorbs water vapor from air to obtain dried air;

moving formulation through pores of a porous membrane in a manner so as to form aerosolized particles wherein the formulation is comprised of a pharmaceutically active drug and a water carrier and the aerosolized particles are drawn into the channel; and continuing to inhale so as to draw the aerosolized particles and dried air into the lungs of a patient.

15. The method of claim 14, wherein the desiccator is selected from the group consisting of $P_2O_5$, $Mg(ClO_4)$, KOH, $H_2SO_4$, NaOH, CaO, $CaCl_2$, $ZnCl_2$, and $CaSO_4$.

16. A disposable container for use in aerosolized delivery of drugs to the lungs, comprising:

a wall which is collapsible upon the application of force;

a porous membrane covering an exit path from the container, the porous membrane having pores with a diameter in the range of about 0.25 to about 6.0 microns the membrane being rigid and having a convex configuration which protrude upward away from the exit path; and a formulation comprised of a pharmaceutically active drug and a carrier which formulation is characterized by its ability to form an aerosol of particles which can be inhaled into a patient's lungs when the formulation is moved through the pores of the membrane.

17. The container of claim 16, wherein the exit path leads to an open channel leading to a breakable seal beyond which is an area covered by the porous membrane.

18. The container of claim 16, wherein the membrane has a thickness in the range of 5 to 200 microns.

19. A disposable package comprising a plurality of interconnected disposable containers as claimed in claim 16.

* * * * *